United States Patent [19]

Hirsch

[11] Patent Number: 6,106,837
[45] Date of Patent: Aug. 22, 2000

[54] METHOD OF TREATING HEADACHES, AND ARTICLE OF MANUFACTURE THEREFOR

[76] Inventor: Alan R. Hirsch, 180 E. Pearson #4702, Chicago, Ill. 60611

[21] Appl. No.: 08/870,160

[22] Filed: Jun. 6, 1997

Related U.S. Application Data

[60] Provisional application No. 60/046,566, May 15, 1997.

[51] Int. Cl.[7] .................. A01N 65/00; A61K 35/78; A61F 13/00
[52] U.S. Cl. ........................... 424/195.1; 424/434
[58] Field of Search .................. 602/74; 424/195.1, 424/434; 512/4, 5; 514/872, 929; 600/557

[56] References Cited

U.S. PATENT DOCUMENTS

| | | |
|---|---|---|
| 4,592,912 | 6/1986 | Nickolaus . |
| 5,008,289 | 4/1991 | Bernstein .......................... 514/535 |
| 5,399,092 | 3/1995 | Olsen ................................ 434/238 |
| 5,468,482 | 11/1995 | Calam et al. . |
| 5,538,959 | 7/1996 | Mauskop ........................... 514/165 |
| 5,554,639 | 9/1996 | Craig et al. ....................... 514/415 |

OTHER PUBLICATIONS

Larry and Elvire van Leewyn–Smith, "Aromatherapy" (1995–1996).
Amoore et al., Rhinology 21:49–54, 1983.
Amoore et al., *Rhinology* 21:49–54 (1983).
Amoore and O'Neill, Proposal for Unifying Scale to Express Olfactory Thresholds and Odor Levels: The "Decismel Scale", in *Proc.of 1988 Air Pollution Control Assn. Annual Mtg.*, Paper No. 78.5 (21 pp.), Air and Waste Management Assn., Pittsburgh, PA (1988).
Amoore and Hautala, *J. Appl. Toxicology* 3(6):272–290 (1983).
Blau, et al., *J. of Neurology*, 232: 275–276 (1985).
Blau, J.N., *The Lancet* 339: 1203 (1992).
Blau, J.N., *Cephalalgia* 13: 293–295 (1993).
Doty et al., *Ann. Neurol.* 25: 166–171 (1989).
Doty, *The Smell Identification Test: Administration Manual* 1983: 13–14, Philadelphia: Sensonics, Inc. (1983).
Gent, in *Clinical Measurement of Taste and Smell*, pp. 107–166, H.L. Meiselman et al. (eds.), 602 pp., MacMillan, NY (1986).
Hirsch and Cain, *Chemical Senses* 17(5): 643 (1992).
Hirsch, Alan R., *Headache* 32: 233–236 (1992).
King, J.R., *Perfumery: The psychology and the Biology of Fragrance*, Van Toller and Dodd (eds.), London: Chapman and Hall, Ltd., pp. 147–165 (1988).
Koss et al., *Neurology* 38: 1228–1232 (1988).
Hirsch, Alan R., *Headache* 32: 262.
Tri–County Eye Physicians & Surgeons, P.C., *Migraine Headaches* (1996).
Stars Media, *The Health Shelf* (1996).
Prevention's Healthy Ideas, *Headaches* (1996–1997).
Larry & Elvire van Leewyn–Smith, *Aromatherapy* (1995–1996).
Juice America, Inc., *Recommendations for Use of Raw Juices* (1996).
Juengling, M., *Product Ingredients* (1997).
Hoosier Herbal Remedies, *The "ENERMED" Treatment for Relief of Migraine Headaches and Multiple Sclerosis* (1997).
Glaxo Wellcome, Inc., *Welcome to the Migraine Resource Center* (1996).
Connections Therapies, *Aromatherapy* (1996).
Hoosier Herbal Remedies, *Herbs Used in KMR Concentrate* (1997).

*Primary Examiner*—Thurman K. Page
*Assistant Examiner*—S. Howard
*Attorney, Agent, or Firm*—Godfrey & Kahn, S.C.

[57] ABSTRACT

A method is provided for preventing or reducing the symptoms and/or duration of a migraine or other form of headache through the administration of a hedonically pleasant odorant that is inhaled by a person who is prone to or suffering from a headache. A preferred odorant is one having the characteristics of a green apple scent. Preferably, the person is presented with the odorant at a suprathreshold concentration, and inhales the odorant for about 5–15 minutes while in a prone position in a quiet, darkened room.

28 Claims, No Drawings

METHOD OF TREATING HEADACHES, AND ARTICLE OF MANUFACTURE THEREFOR

CROSS-REFERENCE TO RELATED APPLICATIONS

This application claims the benefit of U.S. Provisional Application Ser. No. 60/046,566, filed May 15, 1997.

FIELD OF THE INVENTION

The present invention relates to the treatment of headaches by the administration of odorants.

BACKGROUND OF THE INVENTION

Millions of Americans and people worldwide suffer from physically debilitating headaches. Symptoms can last more than an hour, and include a throbbing pain on one side of the head usually around the temple, nausea, blurring of vision, and sensitivity to light, sounds and smells. In about 10% of migraine occurrences, a visual aura such as blind spots, flickering points of light, double vision, or jagged lines, will precede the headache.

It has been speculated that vascular and neurogenic factors are responsible for migraine attacks. Migraines are known to be triggered, for example, by anxiety, shock, tension, fatigue and other stress factors, by menstruation and hormonal-fluctuation, by noise, flickering or bright lights, and by foods such as red wine, chocolate, wheat products, and those that contain additives such as MSG (canned soups, corn chips), tyramine (sour cream, parmesan cheese, soy sauce), and nitrites (cured meats, e.g., bacon, ham).

The aggravating effect of certain odors on migraine headaches has been documented in several studies. Blau and Solomon interviewed fifty migraine patients. Twenty of the fifty patients experienced osmophobia due to a variety of odors ranging from general cooking odor to wash-up liquid odor. Eleven patients reported that similar smells also triggered migraine headaches (Blau, et al., *J. of Neurology*, 232 (1985): 275–276). In another study, perfume and cigarette smoke triggered migraine headaches (Raffaeli, et al., *Functional Neurology* 1 (1986): 275–276). Blau's study on migraine triggers showed that certain foods induced migraines while non-migraine headaches were unaffected by them (Blau, J. N., *The Lancet* 339 (1992): 1203).

Studies have also shown smells to be part of migraine auras. Wolberg and Ziegler have reported a case of a woman who experienced olfactory hallucinations involving decaying animals before experiencing migraines (Wolberg, et al., *Arch. Neurol.* 39 (1982): 392). Crosley and Dhamoon described a mother and her daughter smelling odors similar to burning wood chips as a part of their aura (Crosley, et al., *Archives of Neurology* 40 (1983): 459). Diamond et al. mentions a woman who smelled cigarette smoke before, during and after her migraine headache even though she was not a smoker and was not around anyone who smoked (Diamond S. et al., *N. Engl. J. Med.* 312 (1985): 1390). Three migraine patients in Fuller and Guiloff's study reported smelling peanut butter and cigars (Fuller, et al., *Neurol. Neurosurg. Psych.* 50 (1987): 1688–1690). Morrison and Price found that 13% of their subjects experienced gustatory hallucinations during migraine attacks (Morrison, et al., *Psychology Medicine* 19 (1989): 919–925).

Conventional treatments for migraines are directed to oral medications to prevent the headache or reduce the symptoms. Examples include migraine abortives such as ergotamines and sumatriptan, preventatives such as antidepressants and calcium channel blockers, analgesic pain reducers (Tylenol™), and anti-nausea drugs. The ingestion of herbal solutions and teas has also been suggested, such as those made from feverfew, wood betony, chamomile, valerian root, and others. Also disclosed are various liquid formulations that are dispensed to the nasal cavity or directed to the respiratory passages to prevent recurring headaches (U.S. Pat. Nos. 5,554,639 and 5,008,289). Other treatments involve biofeedback, acupuncture, and meditation.

None of the currently known or used treatments for migraine headaches provide consistently effective therapy for preventing or reducing the pain and other symptoms of a migraine headache. A significant drawback of current treatments is the use of drugs and other chemical substances that must be ingested or applied to mucosal tissue for absorption into the bloodstream.

A survey of 109 migraine patients by Blau revealed that fifty patients could tolerate eating and drinking during migraines. Of the fifty patients, twenty-seven patients reported that eating reduced the severity and the length of migrainous symptoms. Five patients actually reported having cravings for certain foods. The patients in the study ate mostly starchy foods during attacks (Blau, J. N., *Cephalalgia* 13 (1993): 293–295). The reason these foods were effective in reducing headache may have been due to the retronasal smell provided during chewing.

Studies have shown that ambient odors can reduce anxiety and change emotions (King, J. R., *Perfumery: The Psychology and the Biology of Fragrance*, Van Toller and Dodd (eds.), London: Chapman and Hall, Ltd., 1988, pp. 147–165). Schiffman describes a study in which patients were conditioned to associate a certain odor with a relaxed state. Patients were able to reduce the severity of their anxiety episodes by inhaling their designated fragrance (Schiffman, S., *Fragrance:. The Psychology and Biology of Perfume*, Van Toller and Dodd (eds.), London: Elsevier Applied Science, 1992, pp. 57–58). In a study by Hirsch on the relationship of odors and perceptions of room size, the subjects perceived the size of a small booth to the larger after inhaling a scent similar to green apples. Hirsch speculated that the green apple scent reduced the anxiety of being enclosed in a small space and thereby increased the perceived room size (Hirsch, et al., Manuscript 1994: 2).

Therefore, an object of the invention is to provide a means that can be used by an individual to hinder or reduce the effect of a migraine headache that overcomes such shortcomings, and does not require the ingestion or absorption of a drug or other chemical substance into the bloodstream of the user. Another object is to provide an effective but simple means of treating and/or preventing a headache, particularly a severe migraine headache, and other forms of pain. Another object is to provide such means in a form that is readily available for use, and is portable and can be easily carried by the user.

SUMMARY OF THE INVENTION

These and other objects are achieved in a method of preventing or reducing the symptoms and/or duration of a migraine or other form of headache, or other form of pain, through the administration of an odorant that is inhaled by the individual.

The method involves administering an effective concentration of a hedonically positive odorant to an individual who is prone to or suffering from a migraine or other form of headache, and having the individual inhale the odorant for an effective time period to alleviate and/or reduce cephalgic pain and other symptoms of the headache. Preferably, the subject individual is presented with the odorant at a suprathreshold concentration (e.g., about 25–55 decismel units), and inhales the odorant for about 5–15 minutes, preferably about 10 minutes. It is further preferred that the individual inhales the odorant while in a prone position, preferably in a quiet room and one that has subdued lighting or, preferably, is completely darkened.

The odorant that is administered is an aromatic substance to which the individual displays a positive hedonic response (e.g., a pleasing odor), and that provides an anxiety reducing or calming effect on the individual when inhaled. A preferred substance has the characteristics of a green apple odorant.

DETAILED DESCRIPTION OF THE INVENTION

According to the invention, it was found that the administration of a hedonically positive odorant will reduce the severity and/or duration of cephalic pain and other symptoms caused by a migraine or other form of headache. Such an odorant is one to which the individual has a pleasant or positive reaction to its scent.

According to the present method, a hedonically pleasing odorant is presented to an individual for inhaling in an amount and for a time effective to prevent, alleviate and/or reduce migrainous or other headache symptoms, which is a supra-threshold but non-irritant level of the odorant. The concentration of an odorant that is administered is preferably within a range of about 25–55 decismel units.

An example of such an odorant is a substance having the characteristic of a green apple odor such as isoamyl isovalerate. Other useful odorants include, for example, banana, peppermint, and lavender. Such odorants are available commercially, for example, from International Flavors and Fragrances, Inc. (IFF, New York, N.Y.), Energy Essentials, Aroma Tech, and as essential oils.

The odorant can be administered to an individual who is prone to migraines or other forms of headache, and/or experiencing a visual aura prior to or preceding the onset of migraine headache symptoms, as a preventative to eliminate a symptom and/or reduce the severity and/or duration of a symptom. The odorant can also be administered as a therapeutic after the onset of migrainous or other headache symptoms to reduce the severity and/or duration of a symptom.

The individual is instructed to inhale the odorant for an effective time period, preferably about 5–15 minutes, preferably about 10 minutes. It is preferred that the person is lying down in a comfortable, prone position during the inhalation period, most desirably in a room that is quiet or sound-proofed, and dimmed to totally darkened.

The method can also be used in the treatment of other forms of body pain, for example, pain associated with muscle strain, stomach cramps, surgical pain, and the like, to reduce the severity or duration of the pain that is being experienced.

An odorant or odorant mixture can be readily screened and assessed for positive hedonics and effectiveness in alleviating migrainous or other headache symptoms. For example, an odorant or odorant mixture can be administered to an individual who is questioned as to a positive or negative reaction to the pleasantness of the scent. The odorant can then be administered to the individual to assess its effectiveness in alleviating and reducing the headache symptoms.

The effect of an odorant on an individual's migraine or other headache symptoms can be assessed and measured subjectively by interviewing and questioning the individual about their symptoms before and after inhaling the odorant substance. For example, the individual can be asked whether they are experiencing a visual aura (e.g., blind spots, flickering lights, jagged lines), a pain that is more pronounced or severe on one side of the head, a pounding or throbbing head pain, head pain that disrupts their normal activity, head pain that is aggravated by activity, nausea, blurred vision, double vision, or sensitivity to light, sound or smell.

An odorant is presented at a suprathreshold level when the decismel level or concentration of the odorant is beyond that needed to be detected by a normosmic individual. At its irritative level, the odorant quantity is so high and intense that the odorant stimulates predominantly the trigeminal nerve (for pain) rather than the olfactory nerve and, hence, is perceived as noxious or painful. The irritation threshold of the patient is the lowest concentration of the substance that causes immediate stinging or burning sensations in the nose, or stinging or lacrimation of the eye. See, J. F. Gent, in *Clinical Measurement of Taste and Smell*, pages 107–166, H. L. Meiselman et al. (eds.), 602 pp., MacMillan, NY (1986); R. L. Doty et al., *Ann. Neurol.* 25: 166–171 (1989); E. Koss et al., *Neurology* 38: 1228–1232 (1988); and R. Doty, *The Smell Identification Test: Administration Manual* 1983: 13–14, Philadelphia: Sensonics, Inc. (1983).

Preferably, prior to the administration of the odorant, the individual is evaluated for olfactory capacity (e.g. loss of smell) according to an olfactory threshold test as known and used in the art. Such a test provides a precise magnitude of loss of smell and classifies the individual as normosmic, hyposmic or anosmic, which is useful in assessing the effectiveness of a particular odorant and/or the required concentration of the odorant to provide a suprathreshold level to effectively reduce migrainous symptoms. According to that test, an odorant substance such as butyl alcohol, phenyl ethyl alcohol, or pyridine, is combined in a odorless liquid medium to provide a series of dilutions, or binary steps, of the odorant. For each successive binary step up the dilution scale, the odorant is present, for example, at one half the concentration of the preceding step. The highest concentration of the odorant usually provides the substance at an irritant level. The individual is presented with the series of dilutions in ascending order, and is asked to compare each dilution step to at least one control stimulus, such as odorless propylene glycol.

Ranges of the average normal threshold for various odorant substances can be found in the art, for example, Amoore and O'Neill, "Proposal for Unifying Scale to Express Olfactory Thresholds and Odor Levels: The "Decismel Scale"," in *Proceedings of the* 1988 *Air Pollution control Association Annual Meeting*, Paper No. 78.5 (21 pp.), Air and Waste Management Association, Pittsburgh, Pa. (1988); Amoore and Haotala, "Odor as an Aid to Chemical Safety: Odor Thresholds Compared with Threshold Limit Values and Volatiles for 214 Industrial Chemicals in Air and Water Dilution," *J. Appl. Toxicology* 3(6):272–290 (1983).

In the art, a "normosmic" individual is one who can detect the odor of a substance without irritant sensations when the odorant is presented with the range of its average normal threshold. A "hyposmic" or "microsmic" individual has reduced capacity of the olfactory nerve being able to detect an odorant substance by its odor at a concentration, or decismel level, above that of a normosmic individual yet below its irritant concentration level. An "anosmic" individual is one who has essentially no olfactory nerve capacity being unable to detect the odor of the odorant substance, but has trigeminel nerve function, being able to detect an odorant substance by means of irritant, tingling sensations when it is present at an irritant concentration. A patient who is able to detect pyridine vapor by means of irritant, tingling sensations caused by stimulation of the trigeminel nerve, but who cannot distinguish a pyridine odor at a lower concentration without such sensation, is considered to be anosmic having no olfactory nerve sensitivity.

The odorant substance is dispensed to a subject in a form that provides a vaporous emission for inhalation. The odorant substance can be administered in a liquid or solid form contained in a capped vessel, by opening a blister pack or scratch-and-sniff odor patch containing microcapsules of the odorant, as a spray from an aerosol or non-aerosol pump-type spray device, by means of a scented cloth, as a nasal spray, as a cologne or a cream, from a pen-like dispenser containing a liquid form of the odorant, and the like. It is preferred that the odorant is provided in a portable dispenser that is easily transportable and readily accessible by a person in need of relief, for example, a blister pack, booklet of scratch-and-sniff odor patches, pen-type dispenser, and the like.

The odorant substance can be packaged as part of a kit in association with a container such as a vial, jar, pouch, bottle, cloth, aerosolizer, blister pack, and the like, that held an effective amount of the odorant; and written or other form of instructions (e.g., video or cassette tape) of the use of the odorant to treat and/or prevent migraine headaches. The kit can also include a substance and instructions for testing olfactory threshold. The various parts of the kit can be packaged separately and contained within a box or other packaging material.

The invention will be further described by reference to the following detailed example. This example is not meant to limit the scope of the invention that has been set forth in the foregoing description. Variation within the concepts of the invention are apparent to those skilled in the art. The disclosures of the cited references throughout the application are incorporated by reference herein.

EXAMPLE

Use of Green Apple Odorant to Alleviate Headache

Fifty subjects with chronic cephalalgia were asked to rate the severity of their headaches at the onset and 10 minutes into three separate headache episodes. The first and third headache served as non-odor treated control headaches. During the second attack, each subject rated their headaches before and after smelling a green apple fragrance. For those with a normal olfactory ability and positive hedonics for the odorant, inhalation of the green apple odor reduced the severity of the headache as compared to the non-odor treated condition (p<0.03). These results indicate that green apple odorant is useful in the management of chronic headache.

Methods

Subjects. Thirty-three women and seventeen men ranging in age from 18 to 67 (mean 39) volunteered to be the subjects of this Institutional Review Board approved study. Based on their history, each subject's headache was classified into the following modified categories of the Headache Classification Committee of the International Headache Society (Headache Classification Committee of the International Headache Society, *Cephalalgia* 8 (1988 supp) 7: 1–96). traumatic (20 subjects), common migraine (14), atypical cephalalgia (10), muscle contraction (2), costens (1), pseudomotor cerebri (1), TCE headache (1) and mixed headache types (4).

Instrument. The research staff tested the subjects' olfactory ability by determining the minimal concentration of carbinol they were able to detect using Amoore's Carbinol Threshold Test (Amoore et al., *Rhinology* 21:49–54 (1983)). Thirty-one subjects were able to detect the lowest concentration of 25. Seventeen subjects were able to detect the carbinol smell at the concentration of 55 while the remainder only detected an odor at irritant level.

During the second headache episode, each subject used a pen-like device with the tip impregnated with an odor similar to green apples, a component of the Chicago Smell Test (CST) (A. R. Hirsch et al., *Chemical Senses* 18(5): 570–571 (1993); A. R. Hirsch et al., *Chemical Senses* 17(5): 643 (1992)). Each subject also rated the odor hedonics as positive (pleasant), negative or indifferent (unpleasant). Thirty-five subjects didn't like the odor while fifteen rated the odor (negative) to be positive (pleasant).

The University of Illinois School of Public Health provided the statistical analysis of the data using the t-test for correlation for significant difference from zero and the signed-rank test.

Procedure. After the initial olfactory testing, each subject took a home survey sheet to be filled out during three consecutive migraine attacks. The survey sheet included the name, sex, age, type of headaches and olfactory ability of the subject, and provided a section for rating headache severity on a scale of 1–10.

During the first attack, each subject rated the severity of the headache from 1–10 based on their subjective criteria, with "10" being the most pain and "1" being the least pain that one could theoretically experience. Then they laid in a dark quiet room for ten minutes and rated their headaches again.

During the second episode, each subject laid in a dark quiet room while inhaling the green apple fragrance for ten minutes at their normal respiratory rate. The staff instructed the subjects to hold the pen approximately 2 cm. from their noses. Once again, they rated the headache before and after ten minutes. During the third episode, they rated the headache in the same fashion without the green apple odor.

Results

The results are summarized in Table 1 below. Data for the total group of 50 indicated that the green apple odor did not produce statistically significant improvement in symptoms when compared to just resting in a dark quiet room. However, for the subjects who liked the odor, analysis of their data shows a statistically significant reduction in the severity of their migraines (p<0.03).

TABLE 1

| Pt # | Sex | Age | HA Type | Olf. level | Hedonics | HA #1 Pre | HA #1 Post | HA #1 Delta | HA #2 Pre | HA #2 Post | HA #2 Delta | HA #3 Pre | HA #3 Post | HA #3 Delta |
|---|---|---|---|---|---|---|---|---|---|---|---|---|---|---|
| 1 | f | 29 | 1 | 25 | like (L) | 8 | 8 | 0 | 8 | 6 | 2 | 8 | 8 | 0 |
| 2 | f | 46 | 2 | 25 | dislike (D) | 7 | 7 | 0 | 8 | 8 | 0 | 7 | 7 | 0 |
| 3 | m | 52 | 3 | 35 | L | 10 | 10 | 0 | 10 | 1 | 9 | 1 | 9 | −8 |
| 4 | m | 42 | 1 | 25 | D | 7 | 7 | 0 | 6 | 2 | 4 | 6 | 5 | 1 |
| 5 | f | 32 | 2 | 25 | D | 7 | 7 | 0 | 8 | 8 | 0 | 8 | 8 | 0 |
| 6 | f | 44 | 1 | 25 | D | 5 | 5 | 0 | 5 | 2 | 3 | 1 | 1 | 0 |
| 7 | f | 26 | 2 | 25 | L | 5 | 1 | 4 | 6 | 0 | 6 | 4 | 1 | 3 |
| 8 | f | 50 | 3 | 25 | D | 2 | 0 | 2 | 5 | 0 | 5 | 6 | 1 | 5 |
| 9 | m | 41 | 3 | 55 | D | 6 | 5 | 1 | 6 | 7 | −1 | 4 | 4 | 0 |
| 10 | f | 33 | 2 | 25 | D | 2 | 2 | 0 | 2 | 2 | 0 | 2 | 2 | 0 |
| 11 | f | 37 | 3 | 25 | D | 4 | 6 | −2 | 3 | 1 | 2 | 4 | 4 | 0 |
| 12 | f | 37 | 2 | 35 | D | 3 | 3 | 0 | 3 | 3 | 0 | 3 | 3 | 0 |
| 13 | f | 52 | 2 | 35 | D | 4 | 4 | 0 | 2 | 2 | 0 | 2 | 2 | 0 |
| 14 | f | 43 | 2 | 55 | D | 1 | 1 | 0 | 2 | 2 | 0 | 2 | 2 | 0 |
| 15 | f | 49 | 1 | 25 | D | 5 | 5 | 0 | 5 | 5 | 0 | 5 | 5 | 0 |
| 16 | f | 42 | 2 | 35 | D | 4 | 2 | 2 | 7 | 4 | 3 | 3 | 1 | 2 |
| 17 | m | 33 | 1 | 35 | L | 8 | 8 | 0 | 8 | 6 | 2 | 8 | 8 | 0 |
| 18 | m | 36 | 1 | 35 | L | 6 | 6 | 0 | 4 | 4 | 0 | 8 | 8 | 0 |
| 19 | f | 39 | 2 | 25 | D | 2 | 2 | 0 | 2 | 2 | 0 | 2 | 2 | 0 |
| 20 | m | 18 | 1 | 35 | D | 10 | 10 | 0 | 9 | 8 | 1 | 9 | 7 | 2 |
| 21 | f | 53 | 3 | 35 | D | 7 | 7 | 0 | 8 | 7 | 1 | 8 | 8 | 0 |
| 22 | m | 34 | 3 | 35 | D | 4 | 3 | 1 | 3 | 4 | −1 | 3 | 3 | 0 |
| 23 | m | 46 | 4 | 25 | D | 7 | 7 | 0 | 7 | 7 | 0 | 7 | 7 | 0 |
| 24 | f | 40 | 4 | 25 | D | 4 | 4 | 0 | 3 | 3 | 0 | 3 | 3 | 0 |
| 25 | f | 46 | 1,4 | 25 | D | 4 | 4 | 0 | 3 | 3 | 0 | 5 | 5 | 0 |
| 26 | m | 32 | 1 | 25 | L | 8 | 6 | 2 | 10 | 6 | 4 | 7 | 5 | 2 |
| 27 | f | 53 | 1 | 25 | L | 10 | 8 | 2 | 10 | 5 | 5 | 10 | 8 | 2 |
| 28 | f | 49 | 5 | 25 | L | 4 | 4 | 0 | 5 | 5 | 0 | 5 | 5 | 0 |
| 29 | f | 45 | 3 | 25 | D | 8 | 7 | 1 | 7 | 5 | 2 | 8 | 7 | 1 |
| 30 | f | 21 | 6 | 25 | L | 4 | 4 | 0 | 4 | 3 | 1 | 3 | 3 | 0 |
| 31 | f | 34 | 1 | 25 | D | 8 | 3 | 5 | 10 | 7 | 3 | 10 | 5 | 5 |
| 32 | f | 25 | 1 | 25 | D | 5 | 7 | −2 | 3 | 5 | −2 | 3 | 2 | 1 |
| 33 | m | 33 | 1 | 25 | L | 7 | 8 | −1 | 8 | 8 | 0 | 8 | 5 | 3 |
| 34 | f | 31 | 1 | 25 | D | 7 | 7 | 0 | 7 | 8 | −1 | 6 | 5 | 1 |
| 35 | m | 28 | 1 | 25 | D | 8 | 8 | 0 | 7 | 5 | 2 | 8 | 8 | 0 |
| 36 | f | 46 | 2 | 35 | L | 10 | 9 | 1 | 10 | 4 | 6 | 9 | 9 | 0 |
| 37 | f | 32 | 3 | 25 | L | 9 | 9 | 0 | 9 | 10 | −1 | 9 | 9 | 0 |
| 38 | m | 55 | 1 | 25 | D | 8 | 8 | 0 | 8 | 9 | −1 | 8 | 8 | 0 |
| 39 | m | 38 | 1 | 35 | D | 7 | 7.5 | −.5 | 5 | 6.25 | −1.2 | 5.5 | 5.5 | 0 |
| 40 | f | 58 | 3 | 35 | L | 1 | 1 | 0 | 1 | 1 | 0 | 2 | 2 | 0 |
| 41 | f | 27 | 2 | 35 | D | 5 | 7 | −2 | 7 | 9 | −2 | 7 | 7 | 0 |
| 42 | f | 20 | 2,4 | 25 | D | 6 | 5 | −1 | 7 | 7 | 0 | 7 | 7 | 0 |
| 43 | f | 21 | 1 | 25 | D | 7 | 6 | 1 | 7 | 8 | −1 | 8 | 6 | 2 |
| 44 | m | 67 | 7 | 35 | D | 0 | 0 | 0 | 0 | 0 | 0 | 0 | 0 | 0 |
| 45 | m | 25 | 1 | 35 | D | 4 | 4 | 0 | 6 | 4 | 2 | 5 | 5 | 0 |
| 46 | f | 31 | 3 | 35 | D | 5 | 5 | 0 | 4 | 5 | −1 | 6 | 6 | 0 |
| 47 | f | 34 | 2 | 25 | D | 5 | 3 | 2 | 5 | 7 | −2 | 3 | 3 | 0 |
| 48 | f | 46 | 4,5 | 25 | L | 8 | 8 | 0 | 5 | 4 | 1 | 9 | 9 | 0 |
| 49 | m | 18 | 1 | 35 | L | 8 | 4 | 4 | 8 | 2 | 6 | 8 | 5 | 3 |
| 50 | m | 37 | 2,4 | 25 | D | 3 | 5 | −2 | 3 | 3 | 0 | 7 | 7 | 0 |

Headache Types:
1-Traumatic, 2-Common Migraine, 3-Atypical Cephalagia, 4-Muscle Contraction, 5-Costens, 6-Pseudomotor Cerebri, 7-TCE HA, 8-Mixed HA Types.
Positive Delta number indicates improvement in symptoms.

Discussion

The results of this study have great implications for new methods of empiric therapy for migraines. Blau suggests that the eating patterns of the migraine patients in his survey implies that migraine headaches may be triggered in part by deficiency of metabolites. However, the main discussion centers around the therapeutic implications of the survey results. If patients are able to tolerate eating, they should be encouraged to eat starchy foods with their headache medications (Blau, J. N., Cephalalgia 13 (1993): 293–295). Blau overlooks the possibility that the positive effects of food is from the odors that are derived therefrom, as 90% of taste is really smell.

The efficacy of the green apple odor in this study hinged upon hedonics. Those patients who like the smell had a statistically significant reduction in the severity of their headaches while those patients who disliked the smell were not significantly affected by the odor in either a positive or negative manner. Similar hedonically linked effects of odor have been demonstrated in regard to learning ability, obesity, claustrophobia, and evaluation of environmental objects. It has been shown that there is a higher prevalence of hyposmia and anosmia in migraine patients then the general population (Hirsch, Alan R., Headache 32 (1992): 233–236). However, there was no distinction in olfactory ability between the two hedonic groups that might link the reduction of migraine symptoms with better olfactory ability.

The positive response in the fifteen patients may have been due to an organic effect of the odor itself or their psychological response to the odor through Pavlovian conditioning. These patients may have associated the green apple odor with a past anxiety- or pain-alleviating experience that could have helped them to relax during their headache episodes. Alternatively, in a study of "olfactory-evoked recall," it was demonstrated that food smells were the most common olfactory triggers of this response, in which people recalled certain past events after smelling a certain odor (Hirsch, A. R., *Chicago Medicine* 98 (May, 1995): 16–19). These were usually pleasant memories and were associated with a positive mood state. Thus, by inducing the sufferer to be in a more positive mood state, the headache may have been less severe since a positive mood state tends to reduce headache. The lack of response from those who didn't like the smell is a strong indication that the response of the patient to the odor was more important than the actual chemical impregnated in the pen-tips, but does not preclude the possibility of a neurophysiologic effect of the odors. Serotonin (5HT), norepinephrine (NE), (-Amino butyric Acid (GABA), and Substance P are all known to be both neurotransmitters within the olfactory bulb, hence effected by odors, and essential modulators of headache including migraine. The odor may have had its pain relieving effect in a venue similar to pharmacologic agents used in the management of headache (such as amitriptyline or Phoschol) by modifying the actual neurotransmitters involved in the pain pathway. An integration may have occurred such that in those with negative hedonics for the odor, such a strong negative mood state was induced that the neurophysiologic effect of the odor was unable to overcome it and thus had no pain alleviating effect.

The therapeutic implications of a green apple odorant and other hedonically pleasant odorants are clear. In addition to the standard medical treatment of migraines, patients can further benefit from effective adjuvant therapy such as eating certain foods or inhaling certain odors. The use of fragrances in treating migraines provides more options in treatment for those who poorly tolerate standard medical therapy.

What is claimed is:

1. A method of alleviating cephalic pain caused by a headache in a person, consisting essentially of:
   administering to the person by inhalation, a green apple odorant in an amount and for a time period effective to alleviate the cephalic pain; the odorant being hedonically pleasant to the person; wherein a suprathreshold but non-irritant amount of the odorant is administered.

2. The method according to claim 1, wherein the concentration of the odorant is about 25–55 decismel units.

3. The method of claim 1, wherein the cephalic pain is caused by a migraine headache and composed of a pronounced pain on one side of the head, or a throbbing head pain.

4. The method of claim 1, wherein administering the odorant is effective to further alleviate a symptom selected from the group consisting of a visual aura, nausea, blurring of vision, double vision, sensitivity to light, sensitivity to sound, sensitivity to an odor, and a combination thereof.

5. The method of claim 1, further comprising, prior to the administering the odorant:
   evaluating the person for olfactory capacity according to an olfactory threshold test; and
   adjusting the concentration of the odorant to provide a suprathreshold level for administration to the person.

6. The method of claim 1, wherein the odor is administered to the person for inhalation for a time period of about 5–15 minutes.

7. The method of claim 1, wherein the odorant is administered to the person while in a prone position.

8. The method of claim 1, wherein the odorant is administered to the person in a sound-reduced room.

9. The method of claim 1, wherein the odorant is administered to the person in a darkened room.

10. A method for screening an odorant substance for alleviating cephalic pain caused by a migraine headache in a person, comprising:
    administering to the person, an odorant substance for inhalation;
    questioning the person as to whether the odorant is positively or negatively hedonic;
    administering to the person by inhalation the hedonically pleasant odorant in an amount and for a time period effective to alleviate the cephalic pain caused by a migraine headache wherein a suprathreshold but non-irritant amount of the odorant is administered;
    questioning the person as to the effectiveness of the odorant in alleviating the cephalic pain.

11. The method of claim 10, wherein the hedonically pleasant odorant is administered for a time period of about 5–15 minutes.

12. The method of claim 10, further comprising:
    having the person lie down in a prone position during inhalation of the hedonically pleasant odorant.

13. The method of claim 10, further comprising:
    administering the hedonically pleasant odorant in a sound-reduced room, a darkened room, or both.

14. The method of claim 10, further comprising, prior to the administering the odorant substance:
    evaluating the person for olfactory capacity according to an olfactory threshold test; and
    adjusting the concentration of the odorant to provide a suprathreshold but not an irritant amount of the odorant for administration to the person.

15. The method of claim 14, wherein the concentration of an odorant is about 25–55 decismel units.

16. An article of manufacture, comprising, packaged together:
    (a) an odorant as recited in claim 1, wherein the green apple odorant when inhaled by a person is effective to alleviate the cephalic pain of a migraine headache; and
    (b) instructions for use of the odorant according to the method of claim 1.

17. The article of manufacture according to claim 16, wherein the odorant is packaged within a delivery means selected from the group consisting of a vial, jar, pouch, can, box, bottle, blister pack, and a scratch-and-sniff odor patch containing microcapsules of the odorant.

18. The article of manufacture according to claim 16, wherein the odorant is in a form selected from the group consisting of a cloth scented with the odorant, an aerosol spray, a pump spray, a nasal spray, a liquid or solid form of the odorant contained in a vessel having a cap, a liquid or solid form of the odorant contained in a blister pack, and odorant microcapsules contained in a scratch-and-sniff odor patch.

19. The article of manufacture according to claim 16, wherein the odorant is in the form of a cream or a cologne.

20. The article of manufacture according to claim 16, wherein the odorant is in a liquid form contained in a dispenser.

21. The article of manufacture according to claim 20, wherein the dispenser has a tip impregnated with the odorant.

22. A method of alleviating cephalic pain caused by a headache in a person, consisting essentially of:

administering to the person by inhalation a banana or peppermint odorant in an amount and for a time period effective to alleviate the cephalic pain; the odorant being hedonically pleasant to the person; wherein a suprathreshold but non-irritant amount of the odorant is administered.

23. The method of claim 22, wherein administering the odorant is effective to further alleviate a symptom selected from the group consisting of a visual aura, nausea, blurring of vision, double vision, sensitivity to light, sensitivity to sound, sensitivity to an odor, and a combination thereof.

24. An article of manufacture, comprising, packaged together:
   (a) an odorant as recited in claim 22, wherein the odorant when inhaled by a person is effective to alleviate cephalic pain caused by a migraine headache; and
   (b) instructions for use of the odorant according to the method of claim 22.

25. The article of manufacture according to claim 24, wherein the odorant is packaged within a delivery means selected from the group consisting of a vial, jar, pouch, can, box, bottle, blister pack, and a scratch-and-sniff odor patch containing microcapsules of the odorant.

26. The article of manufacture according to claim 24, wherein the odorant is in a form selected from the group consisting of a cloth scented with the odorant, an aerosol spray, a pump spray, a nasal spray, a liquid or solid form of the odorant contained in a vessel having a cap, a liquid or solid form of the odorant contained in a blister pack, and odorant microcapsules contained in a scratch-and-sniff odor patch.

27. A method of alleviating cephalic pain caused by a headache in a person, consisting essentially of:
   determining the character of an odorant as hedonically pleasant or unpleasant by the person, by administering the odorant to the person by inhalation; and
   administering a suprathreshold but non-irritant amount of the hedonistically pleasant odorant to the person, by inhalation for a time period effective to alleviate the cephalic pain.

28. The method of claim 27, wherein the odorant is selected from the group consisting essentially of green apple, banana, and peppermint.

* * * * *

UNITED STATES PATENT AND TRADEMARK OFFICE
CERTIFICATE OF CORRECTION

PATENT NO. : 6,106,837 Page 1 of 1
DATED : August 22, 2000
INVENTOR(S) : Alan R. Hirsch It is certified that error appears in the above-identified patent and that said Letters Patent is hereby corrected as shown below:

<u>Title page,</u>
Item [56], References Cited, U.S. PATENT DOCUMENTS,
Add -- 4,948,781  8/1990  Kaiser et al.  512/25 --

Signed and Sealed this

Second Day of March, 2004

JON W. DUDAS
*Acting Director of the United States Patent and Trademark Office*